United States Patent
Li et al.

(10) Patent No.: US 8,871,217 B2
(45) Date of Patent: Oct. 28, 2014

(54) METHOD FOR PRODUCING FUCOXANTHIN

(75) Inventors: Yanmei Li, Beijing (CN); Liang Li, Beijing (CN)

(73) Assignee: Beijing Gingko Group Biological Technology Co., Ltd., Beijing (CN)

( * ) Notice: Subject to any disclaimer, the term of this patent is extended or adjusted under 35 U.S.C. 154(b) by 364 days.

(21) Appl. No.: 12/619,474

(22) Filed: Nov. 16, 2009

(65) Prior Publication Data

US 2010/0152286 A1 Jun. 17, 2010

(30) Foreign Application Priority Data

Nov. 17, 2008 (CN) .......................... 2008 1 0226391

(51) Int. Cl.
| | | |
|---|---|---|
| A61K 36/02 | (2006.01) | |
| A61K 36/03 | (2006.01) | |
| A61K 36/04 | (2006.01) | |
| A61K 36/05 | (2006.01) | |
| C07D 303/02 | (2006.01) | |
| A61K 31/336 | (2006.01) | |
| C07D 303/14 | (2006.01) | |
| C07D 303/32 | (2006.01) | |

(52) U.S. Cl.
CPC ............... *A61K 31/336* (2013.01); *A61K 36/03* (2013.01); *C07D 303/02* (2013.01); *C07D 303/14* (2013.01); *C07D 303/32* (2013.01); *A61K 36/02* (2013.01)
USPC .................................................... 424/195.17

(58) Field of Classification Search
USPC .................................................... 424/195.17
See application file for complete search history.

(56) References Cited

U.S. PATENT DOCUMENTS

| | | | | |
|---|---|---|---|---|
| 5,502,041 A | * | 3/1996 | Moen et al. ...................... | 514/54 |
| 2008/0089851 A1 | * | 4/2008 | Mekideche ...................... | 424/59 |
| 2010/0210722 A1 | * | 8/2010 | Shin et al. ...................... | 514/546 |

FOREIGN PATENT DOCUMENTS

| | | | | | |
|---|---|---|---|---|---|
| CN | 101249059 | | * | 8/2008 | |
| CN | 101249060 | | * | 8/2008 | |
| CN | 101250232 | | * | 8/2008 | |
| CN | 102321052 | | * | 1/2012 | |
| JP | 54152027 | A | * | 11/1979 | .............. C09B 61/00 |
| JP | 2004-075634 | A | * | 3/2004 | .............. A61K 36/02 |
| JP | 2008255231 | | * | 10/2008 | |
| JP | 2009120494 | | * | 6/2009 | |

OTHER PUBLICATIONS

Innovations United—Industrial and Preparative Resin Catalog. 2011, 26 pages.*

* cited by examiner

*Primary Examiner* — Chris R Tate
(74) *Attorney, Agent, or Firm* — LaRiviere, Grubman & Payne, LLP

(57) ABSTRACT

The present invention provides a method for producing fucoxanthin extract, said method comprising: performing absorption of the fucoxanthin extract by using absorbent and then performing elution to remove heavy metals and arsenic salt contained in the fucoxanthin extract, wherein the absorbent is selected from a group having macroporous resin, polyamide, activated carbon, alumina and a combination thereof. The method for producing fucoxanthin extract according to the present invention, the content of heave metal in the fucoxanthin extract can be reduced, while the content of fucoxanthin in the fucoxanthin extract can increase. In addition, the present invention also provides a fucoxanthin extract obtained by the above method, as well as fucoxanthin products containing the fucoxanthin extract.

4 Claims, No Drawings

METHOD FOR PRODUCING FUCOXANTHIN

PRIORITY CLAIM

This application claims priority to Chinese Patent Application Number 200810226391.3, A Method for Producing Fucoxanthin, filed on Nov. 17, 2008.

BACKGROUND OF THE INVENTION

1. Field of the Invention

The present invention relates to a method for producing fucoxanthin. In particular, the present invention relates to a method for extracting fucoxanthin from botanic material.

2. Description of the Related Art

Fucoxanthin is red brown, which is one of important carotenoids, and has very strong antioxidation effect. Its formula is $C_{42}H_{58}O_6$ and it has the following structural formula:

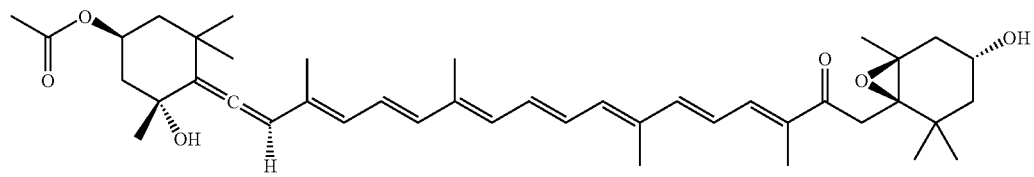

Fucoxanthin, as a kind of carotenoids, is a natural active substance and has high physiological activity. It has very high potential value of development and utilization, as it can regulate blood glucose of the diabetic better, kill lots of cancer (breast cancer, colorectal cancer, prostate cancer and so on) cells, and have very strong antioxidation effect.

However, the content of fucoxanthin in raw material is very low, only 50-100 ppm. Furthermore, this product is powerful antioxidant, thereby it is easily decomposed during producing process. Therefore, its production is very difficult. In addition, the raw material is seaweeds which absorb heave metals and arsenic salt in the sea, thus the obtained extract may contain a large amount of heave metals and arsenic salt during the extraction of fucoxanthin. Therefore, it is always an important problem of the development for fucoxanthin how to reduce the content of heavy metal and arsenic salt during the production of fucoxanthin.

Chinese Patent No. CN1706836 discloses a method for separating fucoxanthin from seaweeds. The detailed operation steps are: washing fresh seaweeds or frozen seaweeds that are thawed at the room temperature with distilled water; then removing water from the surface thereof, and then lixiviating seaweeds by using dimethyl sulfoxide in dark for 15-60 minutes, wherein the amount of dimethyl sulfoxide is 2 ml-6 ml per gram of seaweed. As dimethyl sulfoxide is used as the extraction solvent in this method, the harmful organic solvent is used. Moreover, the boiling point of the solvent is relative high and it is very difficult to remove the organic solvent by conventional operation, therefore the harmful organic solvent will remain in the extract product, so that the product safety is reduced greatly. Furthermore, dimethyl sulfoxide solvent costs much, the production cost is thus increased, and thereby it is not suitable for industrial production. Meanwhile, in the product obtained by the above method, the content of heavy metal and the arsenic salt does thus not accord with the present standard for food additives, which limits the application of this method.

SUMMARY OF THE INVENTION

The present invention aims to solve the above problems existed in the prior art.

The present invention provides a method for producing fucoxanthin extract, which is characterized in comprising: obtaining fucoxanthin extract; performing absorption process of the fucoxanthin extract by using absorbent to reduce the content of heavy metals and arsenic salt contained in the fucoxanthin extract, wherein the absorbent is selected from macroporous resin, polyamide, activated carbon and alumina, and a group including the above.

According to the embodiment of the method for producing fucoxanthin, the content of heavy metals and arsenic salt contained in the fucoxanthin extract can be reduced while the content of fucoxanthin increases after performing absorption process of the fucoxanthin extract by using the absorbent. Therefore, increase of the fucoxanthin content and reduction of the content of heavy metals can be realized at the same time by the producing method of the present invention, which cannot be realized by means of the present producing method.

In the present invention, the fucoxanthin extract is extracted from raw material containing fucoxanthin by an alcohol-water solution. As alcohol-water solution is used for extracting from the raw material to obtain the fucoxanthin crude extract, the extraction efficiency is high and the cost is low. Furthermore, the harmful substances, such as dimethyl sulfoxide, are not used, thereby the safe and edible fucoxanthin extract can be obtained.

In the present invention, the alcohol-water solution has a concentration of 30 vol %-100 vol % and contains alcohols selected from a group including fatty alcohols having 1-4 carbon atoms. The inventor found that the alcohol-water solution of this embodiment has a concentration of 30 vol %-100 vol % and contained alcohols have 1-4 carbon atoms, which can achieve very well extracting effect. In the present invention, the alcohols are selected from a group having ethanol, propanol, isopropanol, butanol and isobutanol, so that production cost can be reduced and extraction efficiency can increase.

In the present invention, the raw material containing fucoxanthin is selected from a group of seaweeds including kelp, gulfweed, fucus, Endarachne binghamiae, Cystin, Chorda filum, *Undaria pinnatifida*, giant kelp, carrageen, *Sargassum kjellmanianum* Yendo, *Sargassum fusiforme*, *Sargassum pallidum* and diatom. The inventor of the present invention found that the content of fucoxanthin in the seaweed (as natural material) is relatively higher than that in other materials, on that the product safety is ensured and production cost is reduced.

In the present invention, the absorbent dealing process is performed by eluting absorbent that absorbed the fucoxanthin extract with alcohol-water solution. As alcohol-water solution is used for elution, the elution efficiency is high and the cost is low. Moreover, the harmful substances such as dimethyl sulfoxide will not be introduced, thereby the edible fucoxanthin extract having high safety can be obtained.

In the present invention, the alcohol-water solution has a concentration of 30 vol %-100 vol %, and the alcohol is selected from a group including alcohols having 1-4 carbon atoms. In this embodiment, the inventor found that it can achieve very good elution effect by using the alcohol-water solution for elution with a concentration of 30 vol %-100 vol %, wherein the contained alcohols have 1-4 carbon atoms. In the present invention, the alcohols are selected from a group including methanol, ethanol, propanol, and isopropanol, preferably ethanol, so that the production cost can be reduced and elution efficiency can increase.

The present invention is composed of a combination of an absorption process and an elution process, wherein the absorption process is performed by absorbing the fucoxanthin extract with the absorbent selected from macroporous resin, polyamide and alumina, and a group including the above, and an elution process is performed by eluting the absorbed fucoxanthin with alcohols. The inventor found that the absorption process of the fucoxanthin extract with the absorbent selected from the group including macroporous resin, polyamide and alumina can achieve both the effect of reducing the content of heave metal and arsenic salt in the fucoxanthin extract and increasing the content of the fucoxanthin in the extract at the same time.

In the present invention, a fucoxanthin extract obtained by the absorption process is also provided. The fucoxanthin extract is safe and can be directly taken by people, as the content of the heave metal in the fucoxanthin extract is low.

In the present invention, a fucoxanthin product containing the fucoxanthin extract obtained by the absorption process is also provided, wherein the content of the heavy metal in the fucoxanthin product is below 10 ppm, and the content of arsenic salt in the same is below 4.0 ppm. The fucoxanthin product is safe and can be directly taken by people, as the content of arsenic salt in the fucoxanthin product is below 4.0 ppm. According to the present invention, the fucoxanthin product is in the form of microcapsule powder, tablet, capsule, particle and pulvis, or is added to food, so that it is ready to serve.

DETAILED DESCRIPTION OF EMBODIMENTS OF THE INVENTION

Hereinafter, the present invention will be described in detail according to the embodiments. However, the embodiments are only used as explanation of the invention rather than limitation thereto.

It shall be indicated that the term "heavy metal" in the description of the present invention includes all metals having influence on human body and contained in fucoxanthin, which include but are not limited to arsenic salt.

The method for producing fucoxanthin of the present invention comprises a method for purification of fucoxanthin.

In the absorption process of the present invention, the fucoxanthin extract is absorbed by the absorbent to remove the heavy metals and arsenic salt contained in the fucoxanthin extract so as to obtain the purified fucoxanthin extract, wherein the absorbent may be selected from macroporous resin, polyamide, activated carbon and alumina, and an appropriate combination thereof.

A conventional purification method can not realize both the increasing of the content of fucoxanthin and removal of heavy metals by eluting the fucoxanthin absorped by the absorbent. In the present invention, however, increasing of the content of fucoxanthin and removal of heavy metals can be realized at the same time by using the above purification method. As a result, the content of heave metal may decrease below 10 ppm, the content of arsenic salt may decrease below 4 ppm, and fucoxanthin extract with high conent can be obtained. In addition, the auxiliary materials used in the production method of the present invention are cheap and the absorbent can be reproduced, which reduces the production cost greatly, thus this method is suitable for mass industrial production.

In the present invention, the edible seaweed is used as raw material, which can insure the safety of the fucoxanthin extract and the safety of the production. In the present invention, the used seaweed is kelp, gulfweed, fucus, Endarachne binghamiae, Cystin, Chorda filum, *Undaria pinnatifida*, giant kelp, carrageen, *Sargassum kjellmanianum* Yendo, *Sargassum fusiforme, Sargassum pallidum* or diatom. It is obvious for those skilled in the art that one kind of plant can be used as raw material, and a combination of a plurality of plants can be also used as the raw material as well. In the present invention, the raw material is crushed before extraction so as to increase the extraction efficiency.

There is no limitation to alcohols in the alcohol-water solution for extraction from seaweeds, as long as fucoxanthin can be extracted from the raw material. In the present invention, the alcohols have 1-4 carbon atoms, which allows few remnants of alcohol remain in the product. In the present invention, the alcohol is selected from a group including ethanol, propanol, isopropanol, butanol and isobutanol, so that the product has few remnants of alcohol, and the extraction efficiency increases. In the present invention, the alcohol-water solution has a concentration of 30 vol %-100 vol %, so that the extraction efficiency is further increased and the extracting time is shortened. It is obvious for those skilled in the art that the alcohol of the alcohol-water solution can use single one alcohol, or a combination of two or more kinds of alcohols.

There is no limitation to the solution used in the absorption process of the fucoxanthin extract with the absorbent. In the present invention, the elution of the fucoxanthin absorbent is performed by using an alcohol-water solution. The alcohol-water solution for extracting process and the alcohol-water solution for the absorption process are independent, that is, an identical solution or different solutions can be used. In the present invention, the alcohol has 1-4 carbon atoms, which allows the product to have few remnants of alcohol. In the present invention, the alcohol is selected from a group including ethanol, propanol, isopropanol, butanol and isobutanol, so that the product has few remnants of alcohol, and the elution efficiency increases remarkably. In the present invention, the alcohol-water solution has a concentration of 30 vol %-100 vol %, so that the elution efficiency is further increased and the elution time is shortened. It is obvious for those skilled in the art that the alcohol-water solution can use single one alcohol, or a combination of two or more kinds of alcohols.

There is no limitation to the sequence of using the absorbents in the absorption process of the fucoxanthin extract with absorbents. Surprisingly, the inventor of the present invention found that when macroporous resin, polyamide, activated carbon, alumina and a group including the appropriate combination of the above are used as absorbents to perform absorption process of the fucoxanthin extract, not only the heave metal, impurities and arsenic salt can be removed, also the content of the fucoxanthin can be increased at the same time.

The present invention provides a fucoxanthin extract obtained according to the above method. The extract accords with the standard of food and is edible as food, as the content of the heave metal in the extract is low.

A fucoxanthin product in any one of the following forms can be further prepared by known methods based on the fucoxanthin containing lowered content of heavy metal and arsenic salt. In the present invention, the fucoxanthin product can be made in the form of microcapsule powder, tablet, capsule, particle or pulvis, or be added to food.

Hereinafter, the method for producing fucoxanthin of the present invention will be further described by specific embodiments. However, the following description is only used as explanation of the invention rather than limitation thereto.

Embodiment 1

Extracting 10 kg of kelp by using 30 L of isopropanol-water solution with 60 vol % at 30° C. for 4 hours, then extracting the residue twice in the same operation, mixing the extracting solution obtained by the first to the third extraction, and passing the mixed solution through a column filled with 5 L of macroporous resin AB-8, performing elution of fucoxanthin by using 15 L of ethanol-water solution with 75 vol %, passing the eluting solution through a column filled with 1 kg of activated carbon, condensing the liquid in a hot water bath of 40° C. during decompression by a rotary evaporator to obtain 1.05 g of red extractum, wherein the content of fucoxanthin is 33 wt %, the content of heavy metal is below 10 ppm, and the content of arsenic salt is 3.01 ppm; solving the red extractum by 9 g of edible oil and 9 g of phospholipid, adding 150 ml of water solution in drops in which 20 g of α-cyclodextrin is solved into the water solution, and emulsifying the same by a emulsion homogenizer at the same time (under nitrogen gas condition), performing drying by a freeze dryer to obtain 35 g of pulvis including fucoxanthin.

Embodiment 2

Extracting 300 g of kelp by using 1350 mL of ethanol-water solution with 50 vol % at 50° C. for 6 hours, then extracting the residue twice in the same operation, mixing the extracting solution obtained by the first to the third extraction, and passing the mixed solution through a column filled with 300 ml of macroporous resin AB-8, performing elution of fucoxanthin by using 30 vol % of ethanol-water solution, passing the eluting solution through a column filled with 100 g of alumina, performing elution of fucoxanthin by using 100 vol % of ethanol-water solution, condensing the eluting solution in a hot water bath of 40° C. during decompression by a rotary evaporator to obtain 0.03 g of red extractum, wherein the content of fucoxanthin is 18 wt %, the content of heavy metal is below 10 ppm, and the content of arsenic salt is 3.61 ppm.

Embodiment 3

Extracting 400 g of Sargassum fusiforme by using 1500 ml of methanol-water solution with 80 vol % at 35° C. for 8 hours, then extracting the residue twice by using 1500 ml of methanol-water solution with 80 vol % at 35° C. for 6 hours, condensing the extracting solutions after being mixed in a hot water bath below 40° C. during decompression by a rotary evaporator to obtain extractum, then filtering the extractum, and solving it by 100 ml of ethanol solution with 80 vol %, and then absorbing fucoxanthin by polycaprolactam, and eluting fucoxanthin by using 95 vol % of ethanol-water solution; adding 10 g of actived carbon into the elution solution, stirring it for 1 hour, filtering, and obtaining 1.02 g of red extractum by the same condensation operations as in examples 1 and 2, wherein the content of fucoxanthin is 18 wt %, the content of heavy metal is below 10 ppm, and the content of arsenic salt is 3.82 ppm; adding the extractum to 70 ml of water solution in which 10 g of dextrin, 10 g of arabic gum and 15 g of lactose are solved, and emulsifying the same by a emulsion homogenizer, and then pressurizing the emulsifier by 200 atmospheric pressure, performing drying by a spray dryer, in which the inlet temperature is set at 140° and the outlet temperature is set at 90° C., and obtaining 31.8 g of microcapsulized powder of fucoxanthin.

Embodiment 4

Extracting 500 g of Undaria pinnatifida by using 2500 ml of ethanol-water solution with 85 vol % at 35° C. for 5 hours, repeating the same operations twice, obtaining extractum after filtering and condensation of the obtained extracing solution, solving the extractum by 75 ml of ethanol-water solution with 85 vol %, passing the solution through a column filled with 25 g of alumina, then eluting the fucoxanthin by using 100 vol % of ethanol-water solution, subjecting the elution solution to the same condensation operations as in examples 1 to 3 to obtain 0.45 g of red extractum, wherein the content of fucoxanthin is 3 wt %, the content of heavy metal is below 10 ppm, and the content of arsenic salt is 3 ppm.

Embodiment 5

Performing the same operations as in example 4, except that the alumina is replaced by 100 ml of macroporous resin AB-8, to obtain the red extractum 0.65 g, wherein the content of fucoxanthin is 10 wt %, the content of heavy metal is below 10 ppm, and the content of arsenic salt is 3.98 ppm.

Embodiment 6

Extracting 500 g of kelp by using 75 vol % of ethanol-water solution at 30° C. for 12 hours, then repeating the above operation twice, passing the obtained extracting solution through a column filled with 100 g of actived carbon (20-60 mesh), condensing the eluting solution in a hot water bath of 40° during decompression by a rotary evaporator to obtain 2.5 g of red extractum after filtering, wherein the content of fucoxanthin is 0.5 wt %, the content of heavy metal is below 10 ppm, and the content of arsenic salt is 3.96 ppm.

What is claimed is:

1. A method for producing a fucoxanthin-enriched seaweed extract, said method comprising:
   a. contacting one or more seaweeds with an alcohol-water extraction solvent to obtain a fucoxanthin extract, and
   b. passing the obtained fucoxanthin extract through an absorbent that absorbs the fucoxanthin extract, then eluting the absorbent with an alcohol-water solution, whereby the content of heavy metals and arsenic salt are reduced and the content of the fucoxanthin is increased in the eluded seaweed extract, wherein the absorbent is selected from the group consisting of macroporous resin, polyamide, alumina, or an appropriate combination thereof,
      wherein the seaweeds are raw materials selected from the group consisting of kelp, gulfweed, fucus, Endarachne binghainize, Cystin, Chorda filum, Undaria pinnatifida, giant kelp, carrageen, Sargassum kjellmanianum Yendo, Sargassum fusiforme, and Sargassum pallidum; and wherein the steps of a and b are not performed in a shaded environment.

2. The method according to claim 1, wherein the extracted solvent comprises an alcohol having 1-4 carbon atoms and a concentration of 30 vol %100 vol %.

3. The method according to claim 1, wherein the solution used to elute the absorbent is an alcohol having 1-4 carbon atoms and a concentration of at least 30 vol %-100 vol %.

4. The method according to claims 1, 2, or 3, wherein the content of heavy metal in the elated seaweed extract is below 10 ppm, and the content of arsenic salt is below 4,0 ppm.

* * * * *

UNITED STATES PATENT AND TRADEMARK OFFICE
CERTIFICATE OF CORRECTION

PATENT NO.         : 8,871,217 B2
APPLICATION NO.    : 12/619474
DATED              : October 28, 2014
INVENTOR(S)        : Yanmei Li et al.

Page 1 of 2

It is certified that error appears in the above-identified patent and that said Letters Patent is hereby corrected as shown below:

In the Specification:
Column 1, line 36, delete "50-100 ppm" and insert --50-100ppm--;
Column 1, line 54, delete "ml-6 ml" and insert --ml-6ml--;
Column 2, line 40, delete "vol %-100 vol %" and insert --vol%-100 vol%--;
Column 3, line 4, delete "vol %-100 vol %" and insert --vol%-100 vol%--;
Column 3, line 34, delete "10 ppm" and insert --10ppm--;
Column 3, line 35, delete "4.0 ppm" and insert --4.0ppm--;
Column 4, line 3, delete "4 ppm" and insert --4ppm--;
Column 5, line 17, delete "10 kg" and insert --10kg--; delete "30 L" and insert --30L--;
Column 5, line 18, delete "vol %" and insert --vol%--;
Column 5, line 22, delete "5 L" and insert --5L--;
Column 5, line 23, delete "15 L" and insert --15L--;
Column 5, line 27, delete "1.05 g" and insert --1.05g--;
Column 5, line 29, delete "3.01 ppm" and insert --3.01ppm--;
Column 5, line 31, delete "150 ml" and insert --150ml--; delete "20 g" and insert --20g--;
Column 5, line 35, delete "35 g" and insert --35g--;
Column 5, line 39, delete "300 g" and insert --300g--; delete "1350 mL" and insert --1350mL--;
Column 5, line 44, delete "300 ml" and insert --300ml--;
Column 5, line 50, delete "0.03 g" and insert --0.03g--;
Column 5, line 52, delete "10 ppm" and insert --10ppm--;
Column 5, line 57, delete "400 g" and insert --400g--; delete "1500 ml" and insert --1500ml--;
Column 5, line 59, delete "1500 ml" and insert --1500ml--;
Column 5, line 64, delete "100 ml" and insert --100ml--;
Column 5, line 67, delete "10 g" and insert --10g--;
Column 6, line 1, delete "1.02 g" and insert --1.02g--;
Column 6, line 4, delete "10 ppm" and insert --10ppm--;
Column 6, line 5, delete "3.82 ppm" and insert --3.82ppm--;
Column 6, line 6, delete first "10 g" and insert --10g--; delete second "10 g" and insert --10g--;
Column 6, line 12, delete "31.8 g" and insert --31.8g--;

Signed and Sealed this
Seventh Day of April, 2015

Michelle K. Lee
*Director of the United States Patent and Trademark Office*

CERTIFICATE OF CORRECTION (continued)
U.S. Pat. No. 8,871,217 B2

In the Specification:
Column 6, line 16, delete "500 g" and insert --500g--; delete "2500 ml" and insert --2500ml--;
Column 6, line 20, delete "75 ml" and insert --75ml--;
Column 6, line 22, delete "25 g" and insert --25g--;
Column 6, line 25, delete "0.45 g" and insert --0.45g--;
Column 6, line 27, delete "10 ppm" and insert --10ppm--; delete "3 ppm" and insert --3ppm--;
Column 6, line 32, delete "100 ml" and insert --100ml--;
Column 6, line 33, delete "0.65 g" and insert --0.65g--;
Column 6, line 35, delete "10 ppm" and insert --10ppm--; delete "3.98 ppm" and insert --3.98ppm--;
Column 6, line 39, delete "500 g" and insert --500g--;
Column 6, line 42, delete "100 g" and insert --100g--;
Column 6, line 47, delete "10 ppm" and insert --10ppm--; delete "3.96 ppm" and insert --3.96ppm--;

In the Claims:
Column 6, line 65, Claim 1, delete "binghainize" and insert --binghamiae--;
Column 7, line 5, Claim 2, delete "vol %100 vol%" and insert --vol% - 100 vol%--;
Column 7, line 10, Claim 4, delete "elated" and insert --eluted--;
Column 7, line 11, Claim 4, delete "10 ppm" and insert --10ppm--; delete "4,0" and insert --4.0--.